US012569180B2

(12) United States Patent
Matsunuma et al.

(10) Patent No.: US 12,569,180 B2
(45) Date of Patent: Mar. 10, 2026

(54) ELECTROCARDIOGRAPHIC SIGNAL MEASUREMENT DEVICE AND ELECTROCARDIOGRAPHIC SIGNAL MEASUREMENT SYSTEM TECHNICAL FIELD

(71) Applicant: MAXELL, LTD., Kyoto (JP)

(72) Inventors: Satoshi Matsunuma, Kyoto (JP); Ayako Shintani, Kyoto (JP); Kazuaki Shimada, Kyoto (JP); Reiji Hattori, Kasuga (JP)

(73) Assignee: MAXELL, LTD., Kyoto (JP)

( * ) Notice: Subject to any disclaimer, the term of this patent is extended or adjusted under 35 U.S.C. 154(b) by 270 days.

(21) Appl. No.: 18/275,824

(22) PCT Filed: Feb. 17, 2022

(86) PCT No.: PCT/JP2022/006396
§ 371 (c)(1),
(2) Date: Aug. 4, 2023

(87) PCT Pub. No.: WO2022/181440
PCT Pub. Date: Sep. 1, 2022

(65) Prior Publication Data
US 2024/0115182 A1     Apr. 11, 2024

(30) Foreign Application Priority Data

Feb. 26, 2021    (JP) ................................. 2021-029621

(51) Int. Cl.
*A61B 5/282*     (2021.01)
*A61B 5/00*     (2006.01)
(Continued)

(52) U.S. Cl.
CPC .............. *A61B 5/282* (2021.01); *A61B 5/256* (2021.01); *A61B 5/277* (2021.01); *A61B 5/308* (2021.01);
(Continued)

(58) Field of Classification Search
None
See application file for complete search history.

(56) References Cited

U.S. PATENT DOCUMENTS 4,263,919 A * 4/1981 Levin ..................... A61B 5/308
600/521
8,938,287 B2 * 1/2015 Felix ..................... A61B 5/308
607/31
(Continued)

FOREIGN PATENT DOCUMENTS

CN     2912512 Y     6/2007
CN     104757964 A     7/2015
(Continued)

OTHER PUBLICATIONS

International Search Report of PCT/JP2022/006396 dated May 10, 2022.
(Continued)

*Primary Examiner* — Carl H Layno
*Assistant Examiner* — Manolis Pahakis
(74) *Attorney, Agent, or Firm* — MATTINGLY & MALUR, PC

(57) ABSTRACT

An electrocardiogram measurement unit comprises: a pair of positive and negative electrode bodies and constituting capacitive coupling electrodes and arranged in a non-contact state with a human body, a signal amplification unit that amplifies an electric signal from both the electrode bodies and outputs the amplified electric signal as an electrocardiographic signal, and an inverting output unit that inverts an (Continued)

in-phase signal of the electric signal from both the electrode bodies and outputs an inverted signal. The electrocardiographic signal measurement device comprises simultaneously both channels and when the electrocardiogram measurement unit to which the inverted signal from the inverting output unit is input to the positive electrode body is defined as a first channel, and the electrocardiogram measurement unit to which the inverted signal from the inverting output unit is input to the negative electrode body is defined as a second channel.

20 Claims, 8 Drawing Sheets

(51) Int. Cl.
| | | |
|---|---|---|
| *A61B 5/256* | (2021.01) | |
| *A61B 5/277* | (2021.01) | |
| *A61B 5/308* | (2021.01) | |
| *A61B 5/318* | (2021.01) | |

(52) U.S. Cl.
CPC ............ *A61B 5/318* (2021.01); *A61B 5/6804* (2013.01); *A61B 5/6891* (2013.01); *A61B 2560/0443* (2013.01); *A61B 2560/0468* (2013.01)

(56) References Cited

U.S. PATENT DOCUMENTS

| | | | | |
|---|---|---|---|---|
| 10,542,900 | B2 * | 1/2020 | Sattler | A61B 5/296 |
| 2003/0073916 | A1 * | 4/2003 | Yonce | A61B 5/30 |
| | | | | 600/509 |

| | | | | |
|---|---|---|---|---|
| 2006/0276702 | A1 * | 12/2006 | McGinnis | A61B 5/296 |
| | | | | 600/372 |
| 2008/0139953 | A1 * | 6/2008 | Baker | A61B 5/024 |
| | | | | 600/509 |
| 2012/0089039 | A1 * | 4/2012 | Felix | A61B 5/346 |
| | | | | 600/523 |
| 2012/0095361 | A1 * | 4/2012 | Xu | A61B 5/305 |
| | | | | 600/300 |
| 2014/0213882 | A1 * | 7/2014 | Chung | A61B 5/0006 |
| | | | | 600/372 |
| 2015/0005585 | A1 * | 1/2015 | Xu | A61B 5/305 |
| | | | | 600/300 |
| 2015/0200637 | A1 | 7/2015 | Ko et al. | |
| 2015/0327815 | A1 * | 11/2015 | Hwang | A61B 5/7225 |
| | | | | 600/547 |
| 2019/0222185 | A1 | 7/2019 | Wang et al. | |
| 2020/0029840 | A1 * | 1/2020 | Nguyen | G16H 40/67 |
| 2020/0245884 | A1 | 8/2020 | Blomqvist | |
| 2023/0000413 | A1 * | 1/2023 | Batzer | A61B 5/28 |

FOREIGN PATENT DOCUMENTS

| | | | |
|---|---|---|---|
| CN | 111132612 | A | 5/2020 |
| CN | 111587533 | A | 8/2020 |
| EP | 3240192 | A1 | 11/2017 |
| JP | 2012-187404 | A | 10/2012 |
| JP | 2013-85753 | A | 5/2013 |
| JP | 2013-150667 | A | 8/2013 |
| JP | 2015-530225 | A | 10/2015 |
| WO | 2014/185532 | A1 | 11/2014 |

OTHER PUBLICATIONS

Chinese Office Action received in corresponding Chinese Application No. 202280010895.X dated Dec. 3, 2025.

* cited by examiner

ELECTROCARDIOGRAPHIC SIGNAL MEASUREMENT DEVICE AND ELECTROCARDIOGRAPHIC SIGNAL MEASUREMENT SYSTEM TECHNICAL FIELD

TECHNICAL FIELD

The present invention relates to an electrocardiographic signal measurement device that measures an electrocardiographic signal related to a heartbeat, and an electrocardiographic signal measurement system including the electrocardiographic signal measurement device.

BACKGROUND ART

In recent years, there is an increasing need to measure an electrocardiographic signal under various environments. For example, an average age of drivers in a transportation industry in 2019 in Japan is around 50 years old, which is 10 years old higher than average ages in all industries, and accordingly, there is a tendency to increase accidents during operation caused by underlying diseases of circulatory systems. Therefore, although a driver's health condition is checked at a company office or the like before operation, it is difficult to grasp a change in physical condition during operation (traveling) of a vehicle, and it is desired in the transportation industry to measure electrocardiographic signals during operation. In addition, there is an increasing need to manage physical conditions of employees in an office environment such as a clerical staff in a company. For example, if an electrocardiographic signal (electrocardiographic waveform) of a driver who is driving a vehicle or an employee who is working is analyzed, then it is possible to calculate an index related to an autonomic nerve of a person to be measured, and thus, it is possible to analyze an index related to a symptom of a disease, or a sympathetic nerve such as fatigue or stress from the index. These indices are useful for detecting chronic fatigue and stress due to work or the like.

In addition, cerebral infarction with an unknown embolic source, a cause of which has been increasing in recent years has not been clarified, accounts for about 30% of a total number of people who develop cerebral infarction, and in recent studies, a possible trigger for the cerebral infarction is considered to be atrial fibrillation of a heart. Atrial fibrillation is a symptom in which the atrium vibrates finely like a spasm and blood cannot be properly sent out, and it is said that when a heart causes atrial fibrillation, a thrombus is easily formed in the atrium, and when a part of the thrombus is carried to a brain and clogs a cerebral blood vessel, cerebral infarction occurs. Although it is possible to measure a change in heart rates (beating rate per minute) over time by measuring electrocardiographic signals of the person to be measured, it is necessary to continuously measure the electrocardiographic signals for a long time in order to detect paroxysmal atrial fibrillation.

However, the person to be measured is not in a resting state in an environment on a vehicle or in an office, and it is necessary to consider an operation such as driving and an influence of electrical environmental noise when performing an electrocardiogram measurement. Further, it is necessary to reduce a physical burden on the person to be measured for measuring electrocardiographic signals for a long time. Therefore, Patent Literature 1 discloses that an electrocardiographic signal is measured using a capacitive coupling electrode that does not need to be directly attached to a surface of a body. Patent Literature 1 proposes an electrocardiogram measurement device (electrocardiographic signal measurement device) comprising two sets of electrodes: a direct electrode provided on a steering wheel of a vehicle and configured to detect a body potential (electric signal) of a driver by being in contact with a skin of a palm of the driver; and a capacitive coupling electrode provided on a seat of the vehicle and configured to detect the body potential of the driver in an electrically insulated state; and an electrocardiograph measuring machine configured to measure an electrocardiographic signal of the driver based on a potential detected by the direct electrode and a potential detected by the capacitive coupling electrode.

CITATIONS LIST

Patent Literature

Patent Literature 1: JP 2013-85753 A

SUMMARY OF INVENTION

Technical Problems

However, in the electrocardiographic signal measurement device in which the direct electrode that is in direct contact with the skin and the capacitive coupling electrode that is not in direct contact with the skin are used in combination as in Patent Literature 1, since the contact state and the contact area between the steering wheel and the skin of the palm always change, it is inevitable that an intensity of the electrocardiographic signal measured by the direct electrode frequently changes or the electrocardiographic signal is intermittent, and it is difficult to stably measure the electrocardiographic signals in the direct electrode. In particular, in a business vehicle such as a truck, a bus, or a taxi, a steering wheel is hardly always gripped with both hands, and in a large vehicle having many manual vehicles, the steering wheel is basically in contact with one hand. In addition, the steering of a large vehicle is often operated by an operation method called a so-called feed handle, and the contact state of the skin changes little by little in the operation.

In the verification of the electrocardiographic signal measurement performed by the present inventors at the time of driving a large vehicle, the time during which the electrocardiographic signal could be measured by the direct electrode of the steering wheel during traveling was 10% or less within the verification time, and the electrocardiographic signal could hardly be measured by the direct electrode. In addition, when the body is twisted with the steering wheel released, the buttocks are lifted from the seat, and it has been seen that no electrocardiographic signal could be measured at all. As described above, according to the verification of the present inventors, it has been found that it is difficult to stably measure the electrocardiographic signal in the electrocardiographic signal measurement device of Patent Literature 1. In addition, when the body is greatly moved such as by operating the steering wheel, noise increases, and it could be difficult to obtain a clear electrocardiographic signal waveform.

An object of the present invention is to provide an electrocardiographic signal measurement device capable of stably measuring an electrocardiographic signal and obtaining a clear electrocardiographic signal while suppressing noise.

Another object of the present invention is to provide an electrocardiographic signal measurement device capable of measuring an electrocardiographic signal while suppressing a physical burden during operation of a vehicle or during work in a seated posture in an office environment.

Another object of the present invention is to provide an electrocardiographic signal measurement system capable of easily confirming an electrocardiographic signal of a person to be measured from a remote position.

Solutions to Problems

The present invention is directed to a multi-channel electrocardiographic signal measurement device comprising a plurality of electrocardiogram measurement units 13 that measure electrocardiographic signals. Each of the electrocardiogram measurement units 13 comprises: a pair of positive and negative electrode bodies 20 and 21 constituting capacitive coupling electrodes and arranged in a non-contact state with a human body; a signal amplification unit 23 that amplifies an electric signal from both the electrode bodies 20 and 21 and outputs the amplified electric signal as an electrocardiographic signal; and an inverting output unit 28 that inverts an in-phase signal of the electric signal from both the electrode bodies 20 and 21 and outputs an inverted signal. The inverted signal output from the inverting output unit 28 is input to any one of the positive and negative electrode bodies 20 and 21. Then, when the electrocardiogram measurement unit 13 to which the inverted signal from the inverting output unit 28 is input to the positive electrode body 20 is defined as a first channel 13A, and the electrocardiogram measurement unit 13 to which the inverted signal from the inverting output unit 28 is input to the negative electrode body 21 is defined as a second channel 13B, it is a feature that both the channels 13A and 13B are simultaneously comprised.

The electrocardiographic signal measurement device has a base 7 that supports a human body or is worn on the human body, and to which the electrode bodies 20 and 21 are attached. As an arrangement of the electrode bodies 20 and 21 at this time, as shown in FIG. 3, a mode can be employed in which the positive electrode bodies 20 (20A and 20B) of the first and second channels 13A and 13B are arranged at one offset position in a left and right direction with respect to a reference line R1 running in an up and down direction of the base 7; the negative electrode bodies 21 (21A and 21B) of the first and second channels 13A and 13B are arranged at the other offset position in the left and right direction with respect to the reference line R1; and the positive and negative electrode bodies 20A and 21A of the first channel 13A, and the positive and negative electrode bodies 20B and 21B of the second channel 13B are alternately arranged in the up and down direction. Note that the expression "alternately arranged" is not limited to the mode in which the channels are arranged in two rows as illustrated in FIG. 3, but is a concept including a mode in which the channels are arranged in three or more rows. The same applies to the following claims.

As an arrangement of other electrode bodies 20 and 21, as shown in FIG. 9, a mode can be employed in which the positive electrode bodies 20 (20A and 20B) for constructing the first and second channels 13A and 13B are arranged at one offset position in an up and down direction with respect to a reference line R2 running in a horizontal direction of the base 7; the negative electrode bodies 21 (21A and 21B) for constructing the first and second channels 13A and 13B are arranged at the other offset position in the up and down direction with respect to the reference line R2; and the positive and negative electrode bodies 20A and 21A for constructing the first channel 13A, and the positive and negative electrode bodies 20B and 21B for constructing the second channel 13B are alternately arranged in the left and right direction.

The electrocardiogram measurement unit 13 comprises a noise removal unit 24 that removes noise included in the electrocardiographic signal output from the signal amplification unit 23.

The base 7 is a backrest 10 of a chair 8, and positive and negative electrode bodies 20 and 21 of the electrocardiogram measurement unit 13 are provided on a front surface of the backrest 10.

The base 7 is an upper garment 33 which is worn on an upper half of a human body, and the positive and negative electrode bodies 20 and 21 of the electrocardiogram measurement unit 13 are provided on this upper garment 33.

An electrocardiographic signal measurement system of the present invention comprises: the electrocardiographic signal measurement device 2 described above that measures an electrocardiographic signal; a recording server 3 that is connected to the electrocardiographic signal measurement device 2 via a communication line 5 and records the electrocardiographic signal measured by the electrocardiographic signal measurement device 2; and a terminal device 4 that is connected to the recording server 3 via the communication line 5 and is capable of acquiring the electrocardiographic signal recorded in the recording server 3. Then, the electrocardiographic signal measurement device 2 is featured by comprising a wireless communication unit 16 for establishing wireless communication with the communication line 5.

Advantageous Effects of Invention

In the electrocardiographic signal measurement device of the present invention, which comprises the inverting output unit 28 that inverts the in-phase signal of the electrical signal from both the positive and negative electrode bodies 20 and 21 constituting the capacitive coupling electrodes and outputs the signal as the inverted signal, the inverted signal output from the inverting output unit 28 is input to any one of the positive and negative electrode bodies 20 and 21. According to this idea, the electrical signal from the electrode bodies 20 and 21 on which noise is superimposed is inverted by the inverting output unit 28 and fed back as the inverted signal to the human body via the electrode bodies 20 and 21, so that a noise reduction effect by a so-called right foot drive (RLD) method is exerted, and thus a clearer electrocardiographic signal can be obtained. In addition, for example, in a mode in which an electrode body dedicated to the RLD is provided in addition to both the positive and negative electrode bodies 20 and 21, there is a possibility that the noise reduction effect by the RLD method is lost when a contact state between the electrode body dedicated to the RLD and a human body is released or the electrode body dedicated to the RLD is greatly separated from the human body. However, when the inverted signal is provided to the electrode bodies 20 and 21 constituting the capacitive coupling electrodes for measuring an electrocardiographic signal as in the present invention, the noise reduction effect by the RLD method is more stably exhibited without being affected by the contact state of the electrode body dedicated to the RLD or the like as described above, so that more stable and clear electrocardiographic signal can be obtained.

In addition, when the electrocardiogram measurement unit 13 in which the inverted signal from the inverting output unit 28 is input to the positive electrode body 20 is defined as the first channel 13A, and the electrocardiogram measurement unit 13 in which the inverted signal from the inverting output unit 28 is input to the negative electrode body 21 is defined as the second channel 13B, if both the channels 13A and 13B are comprised at the same time, the inverted signals can be applied to both the positive and negative electrode bodies 20 and 21 at the same time in one electrocardiographic signal measurement device. Therefore, the noise reduction effect by the RLD method is more reliably exhibited, and a clearer electrocardiographic signal can be obtained, as compared with a mode in which the inverted signal is applied only to one of the electrode bodies 20 and 21.

As the arrangement of the electrode bodies 20 and 21 in the base 7 that supports the human body or is worn on the human body, it is desirable to employ a mode shown in FIG. 3. Specifically, it is desirable to employ a mode that the positive electrode bodies 20 (20A and 20B) of the first and second channels 13A and 13B are arranged at one offset position in the left and right direction with respect to the reference line R1 running in the up and down direction of the base 7; the negative electrode bodies 21 (21A and 21B) of the first and second channels 13A and 13B are arranged at the other offset position in the left and right direction with respect to the reference line R1; and also the positive and negative electrode bodies 20A and 21A for constructing the first channel 13A and the positive and negative electrode bodies 20B and 21B for constructing the second channel 13B are alternately arranged in the up and down direction. According to this mode, the positive and negative electrode bodies 20 and 21 to which the inverted signals are applied do not deviate to any one of the left and right and the up and down, and the inverted signals can be applied to a wider range of the human body, so that the noise can be further reduced and the SN ratio can be improved. Therefore, the electrocardiographic signals can be stably measured, and the clearer electrocardiographic signals can be obtained. Since the arrangement directions of the positive and negative electrode bodies 20 and 21 of the first and second channels 13A and 13B are made to coincide with each other, it is possible to detect the electric signals having the same phase in both the channels 13A and 13B.

The arrangement of the electrode bodies 20 and 21 in the base 7 can also employ a mode shown in FIG. 9. Specifically, a mode can be employed in which the positive electrode bodies 20 (20A and 20B) for constructing the first and second channels 13A and 13B are arranged at one offset position in the up and down direction with respect to the reference line R2 running in the horizontal direction of the base 7; the negative electrode bodies 21 (21A and 21B) for constructing the first and second channels 13A and 13B are arranged at the other offset position in the up and down direction with respect to the reference line R2; and the positive and negative electrode bodies 20A and 21A for constructing the first channel 13A, and the positive and negative electrode bodies 20B and 21B for constructing the second channel 13B are alternately arranged in the left and right direction. In also this mode, the positive and negative electrode bodies 20 and 21 to which the inverted signals are applied do not deviate to any one of the left and right and the up and down, and the inverted signals can be applied to a wider range of the human body, so that the noise can be further reduced and the SN ratio can be improved. Accordingly, the electrocardiographic signal can be stably measured, and the clearer electrocardiographic signal can be obtained. Since the arrangement directions of the positive and negative electrode bodies 20 and 21 of the first and second channels 13A and 13B are made to coincide with each other, it is possible to detect the electric signals having the same phase in both the channels 13A and 13B.

If the electrocardiogram measurement unit 13 comprises the noise removal unit 24 that removes noise included in the electrocardiographic signal output from the signal amplification unit 23, since it is possible to remove the noise from the electrocardiographic signal amplified by the signal amplification unit 23, it can be contributed to clarify the electrocardiographic signal.

If the base 7 is the backrest 10 of the chair 8, and the positive and negative electrode bodies 20 and 21 of the electrocardiogram measurement unit 13 are provided on the front surface of the backrest 10, then the person to be measured can measure his/her electrocardiographic signal only by sitting on the chair 8 and leaning against the backrest 10. Therefore, it is possible to stably measure an electrocardiographic signal of a driver who is driving a vehicle or an employee who is working in an office under the condition that a physical burden is further suppressed.

If the base 7 is an upper garment 33 worn on an upper half body of a human body, and the positive and negative electrode bodies 20 and 21 of the electrocardiogram measurement unit 13 are provided on this upper garment 33, the positive and negative electrode bodies 20 and 21 can be disposed in the body portion only by wearing the upper garment 33, so that the burden on the person to be measured can be suppressed even if the electrocardiographic signal is measured for a long time. In addition, there is also an advantage that the electrocardiographic signals can be measured even in driving of a vehicle, or the like without limitation of behavior.

An electrocardiographic signal measurement system of the present invention is configured by comprises: the electrocardiographic signal measurement device 2 described above that measures an electrocardiographic signal; a recording server 3 that is connected to the electrocardiographic signal measurement device 2 via a communication line 5 and records the electrocardiographic signal measured by the electrocardiographic signal measurement device 2; and a terminal device 4 that is connected to the recording server 3 via the communication line 5 and is capable of acquiring the electrocardiographic signal recorded in the recording server 3, in which the electrocardiographic signal measurement device 2 comprises a wireless communication unit 16 that establishes wireless communication with the communication line 5. According to this idea, since the electrocardiographic signal of the person to be measured can be monitored remotely, for example, when the person to be measured is a driver of a truck or a bus, the electrocardiographic signal during operation of the vehicle can be easily checked at a remote place such as a company office.

BRIEF DESCRIPTION OF DRAWINGS

DESCRIPTION OF EMBODIMENTS (First embodiment) FIGS. 1 to 6 illustrate a first embodiment of an electrocardiographic signal measurement device and an electrocardiographic signal measurement system constructed by including the same measurement device according to the present invention. Front and rear, left and right, and up and down in the present embodiment follow the cross arrows illustrated in FIG. 3 and front and rear, left and right, and up and down displayed in the vicinity of each arrow. In FIG. 2, an electrocardiographic signal measurement system 1 is configured by an electrocardiographic signal measurement device 2 that measures an electrocardiographic signal, a system server (recording server) 3 that records the electrocardiographic signal obtained by the electrocardiographic signal measurement device 2, a terminal device 4 that can acquire data of the electrocardiographic signal recorded in the system server 3, and the like. The system server 3 and the terminal device 4 are connected to a communication line 5 such as the Internet and can communicate with each other. The terminal device 4 is configured by a so-called notebook personal computer.

In FIG. 3, reference numeral 8 denotes a seat (chair) of a vehicle such as a truck, a bus, or a taxi on which a person to be measured sits. The seat 8 includes a seat surface 9 for receiving buttocks and a backrest 10 (base 7) for receiving a body portion. In the present embodiment, the electrocardiographic signal measurement device 2 is provided on the backrest 10. When the electrocardiographic signal measurement device 2 is provided in the seat 8 of the vehicle as described above, an electrocardiographic signal of a person to be measured (for example, a driver of a truck) seated on the seat 8 can be measured. Note that the chair 8 may be an office chair or a seat chair in addition to the seat of the vehicle, and in short, may be any chair on which the person to be measured sits and has his/her back. When the chair 8 is an office chair, it is possible to measure an electrocardiographic signal of a person to be measured (for example, a clerical worker in a company) seated on the office chair.

As illustrated in FIG. 1, the electrocardiographic signal measurement device 2 comprises: two electrocardiogram measurement units 13 and 13 that measure electrocardiographic signals; an analog-digital conversion unit 15 (hereinafter, simply referred to as an A/D converter 15) that converts electrocardiographic signals constructed of analog voltage-modulated signals (hereinafter, simply referred to as analog signals) measured by the electrocardiogram measurement units 13 and 13 into electrocardiographic signals constructed of digital signals; a wireless communication unit 16 that establishes wireless communication between the electrocardiographic signal measurement device 2 and the communication line 5; and a power supply unit 17 that supplies driving power to the electrocardiogram measurement units 13 and 13 and the wireless communication unit 16, and the like. The wireless communication unit 16 can be configured by wireless communication of the IEEE 802.15.1 standard which is a short-distance wireless communication standard, wireless communication of a cellular system (mobile phone communication network), or the like. The power supply unit 17 is preferably configured by a primary battery or a secondary battery. Note that the power supply unit 17 may be an on-vehicle battery in a case where the driving power can be supplied from the on-vehicle battery, and the power supply unit 17 may be a commercial power supply in a case where the chair 8 is an office chair or the like installed in a room and the driving power can be supplied from the commercial power supply.

Figure 1:
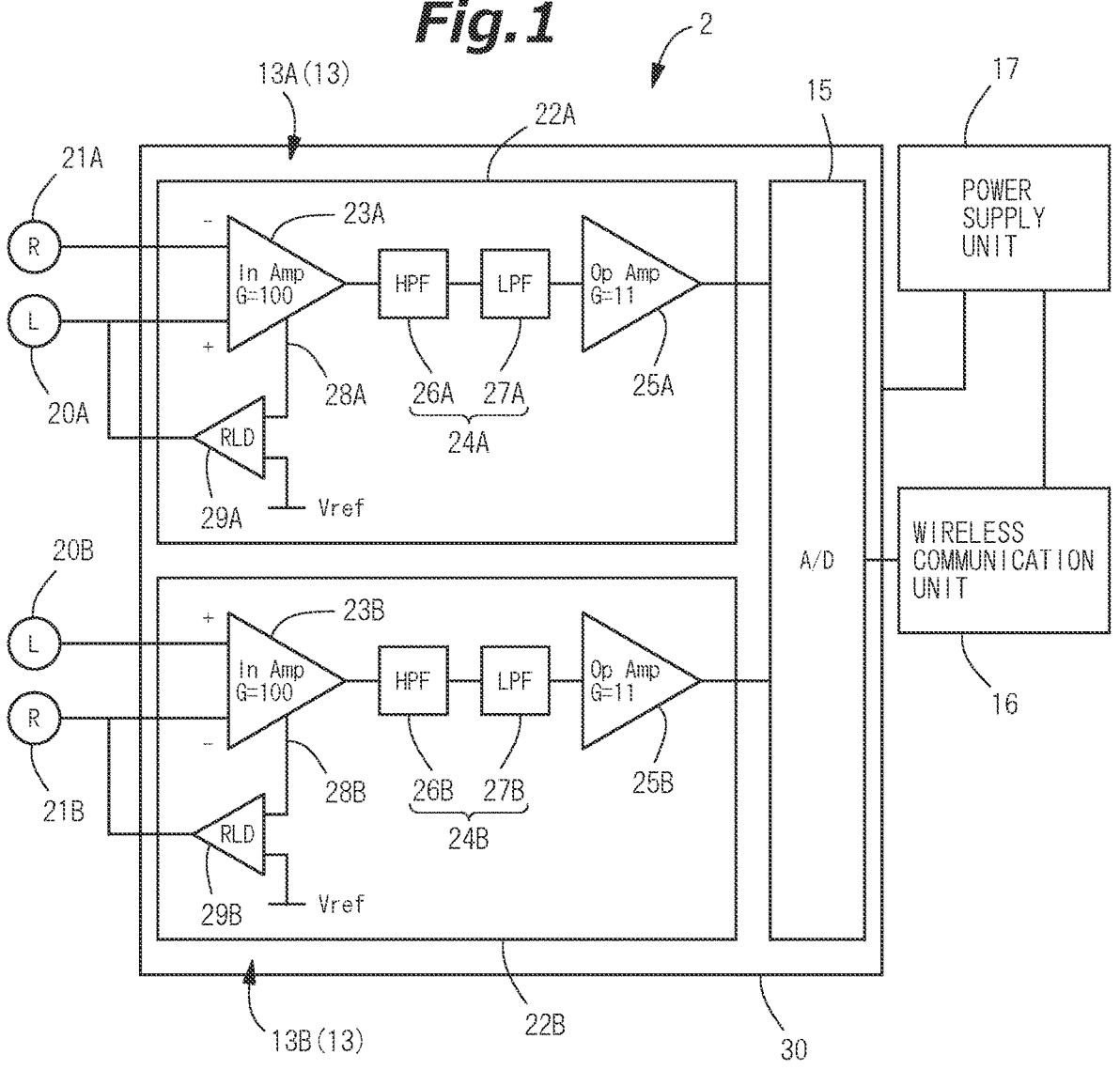
FIG. 1 is a block diagram illustrating an entire electrocardiographic signal measurement device according to a first embodiment of the present invention.
Figure 2:
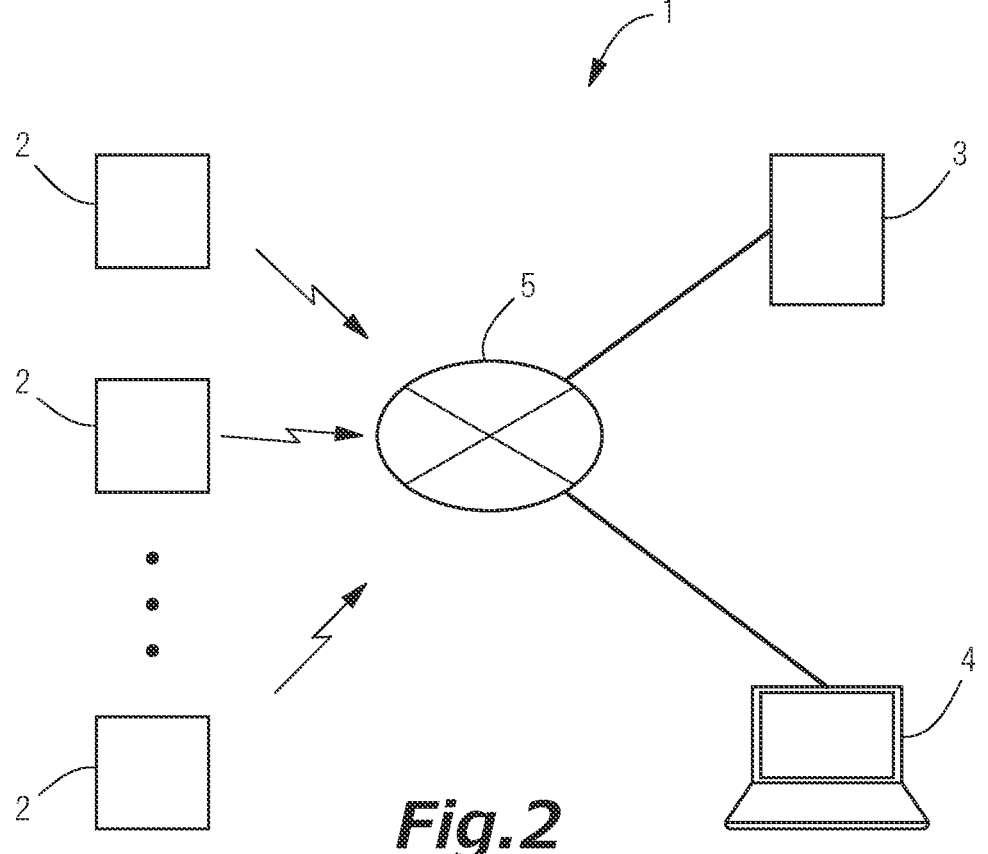
FIG. 2 is a conceptual diagram illustrating an entire electrocardiographic signal measurement system constructed by including the electrocardiographic signal measurement device.

As will be described later, in the two electrocardiogram measurement units 13 and 13, electrode bodies 20 and 21 to which inverted signals are input are different in positive and negative electrode bodies. Here, the electrocardiogram measurement unit 13 to which the inverted signal is applied to the positive electrode body 20 is defined as a first channel 13A, and the electrocardiogram measurement unit 13 to which the inverted signal is applied to the negative electrode body 21 is defined as a second channel 13B. Since basic structures of the electrocardiogram measurement units 13 of both the channels 13A and 13B are the same, the same members are denoted by the same numeral signs, and the description thereof will be omitted. However, "A" is added to an end of a reference numeral of a member constituting the electrocardiogram measurement unit 13 related to the first channel 13A. Similarly, "B" is added to an end of a reference numeral of a member constituting the electrocardiogram measurement unit 13 related to the second channel 13B.

In FIG. 1, the electrocardiogram measurement unit 13 according to the first channel 13A comprises a pair of positive and negative electrode bodies 20A (20) and 21A (21) made of capacitive coupling electrodes that detect an electrical signal of a body portion of a body, and a signal processing unit 22A (22) that processes the electrical signal detected by the positive and negative electrode bodies 20A and 21A to obtain an electrocardiographic signal. The signal processing unit 22A comprises an instrumentation amplifier (signal amplification unit) 23A (23) to which the positive and negative electrode bodies 20A and 21A are connected, a noise removal unit 24A (24) that removes noise included in an electrocardiographic signal output from the instrumentation amplifier 23A, a differential amplifier 25A (25) that amplifies and outputs the electrocardiographic signal after noise removal, and the like. The positive electrode body 20A is connected to a positive input terminal of the instrumentation amplifier 23A, and the negative electrode body 21A is connected to a negative input terminal of the instrumentation amplifier 23A. The noise removal unit 24A removes line noise and interference noise included in an electrocardiographic signal output from the instrumentation amplifier 23A, and is configured by a high-pass filter 26A (26) and a low-pass filter 27A (27).

The instrumentation amplifier 23A comprises an inverting output unit 28A (28) that inverts in-phase signals of electric signals input from the positive and negative electrode bodies 20A and 21A, and outputs the in-phase signals as inverted signals. The inverting output unit 28A is connected to one input terminal of a feedback amplifier 29A (29). A reference voltage circuit is connected to the other input terminal of the feedback amplifier 29A, and an output terminal of the feedback amplifier 29A is connected to the positive electrode body 20A. In the present embodiment, an output terminal of the feedback amplifier 29A is connected to a cable that connects the positive electrode body 20A and the instrumentation amplifier 23A. Note that the output terminal of the feedback amplifier 29A may also be directly connected to the positive electrode body 20A.

In the electrocardiogram measurement unit 13 related to the other second channel 13B, an output terminal of a feedback amplifier 29B (29) is connected to a cable for connecting the negative electrode body 21B and the instrumentation amplifier 23B. Note that the output terminal of the feedback amplifier 29B may also be directly connected to the negative electrode body 21B.

The signal processing units 22A and 22B and the A/D converter 15 constituting both the electrocardiogram measurement units 13 and 13 are fixed to a lower center of a rear surface of a backrest 10 while being accommodated in an electrocardiogram measurement circuit box 30. Also, the previous wireless communication unit 16 and the power supply unit 17 are fixed to a left and a right of the electrocardiogram measurement circuit box 30 (see FIG. 3).

Figure 3:
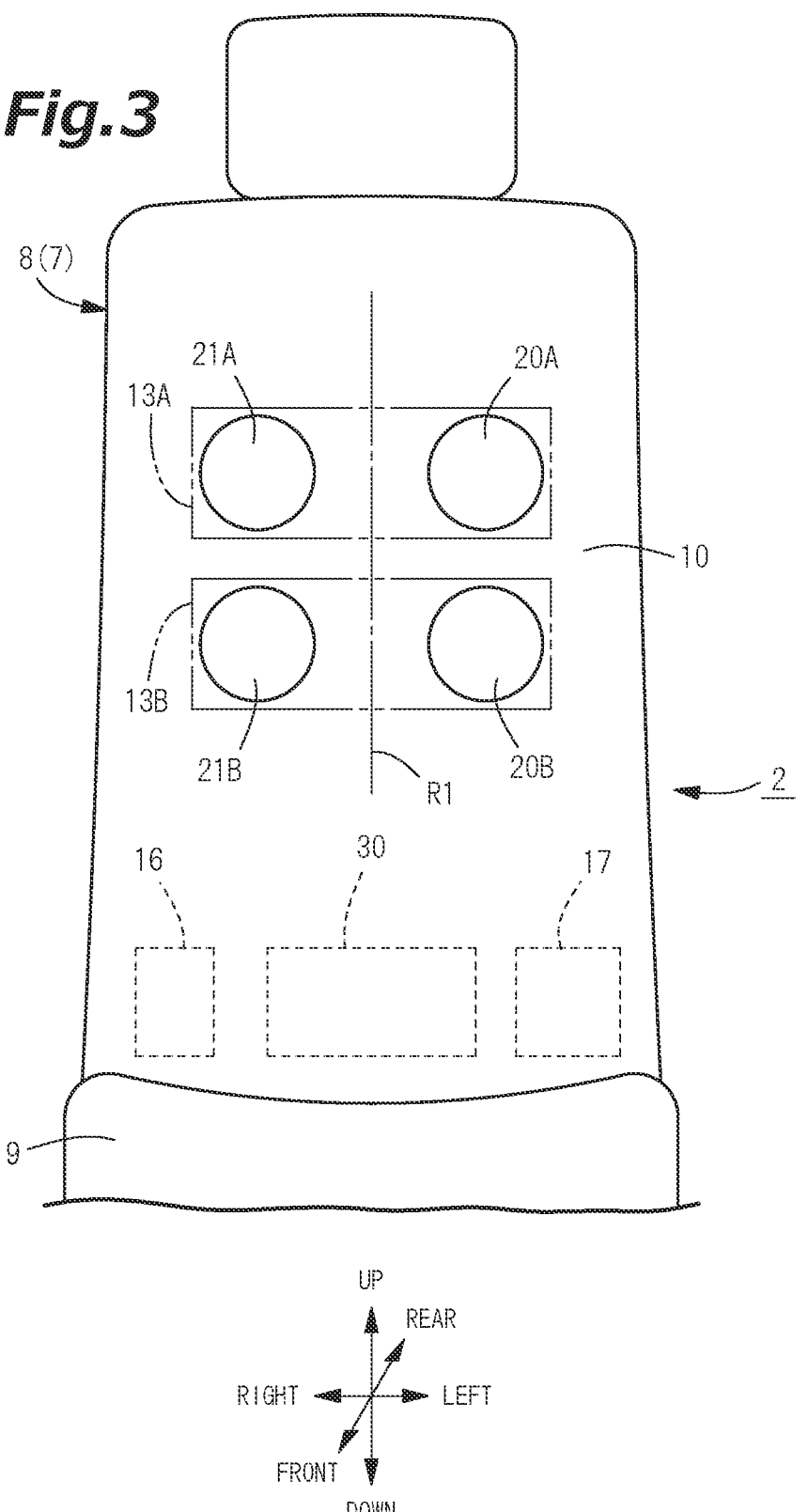
FIG. 3 is a front view illustrating a mode in which the electrocardiographic signal measurement device is provided on a chair.

As shown in FIG. 3, the positive and negative electrode bodies 20 (20A and 20B) and 21 (21A and 21B) related to the first and second channels 13A and 13B are each formed in a disk shape and fixed to a front surface of the backrest 10. The positive electrode body 20A of the first channel 13A is disposed on an upper left side of the backrest 10, and the negative electrode body 21A is disposed on an upper right side of the backrest 10. The positive electrode body 20B of the second channel 13B is disposed on a lower left side of the backrest 10, and the negative electrode body 21B is disposed on a lower right side of the backrest 10.

In addition, as shown in FIG. 3, in the first channel 13A located on the upper side, height positions of the positive and negative electrode bodies 20A and 21A constituting the relevant channel 13A are set to substantially the same position. Similarly, in the second channel 13B located on the lower side, height positions of the positive and negative electrode bodies 20B and 21B constituting the relevant channel 13B are set to substantially the same position. As described above, in the backrest 10, the positive and negative electrode bodies 20A and 21A of the first channel 13A and the positive and negative electrode bodies 20B and 21B of the second channel 13B are arranged side by side in a vertical direction. Also, the positive and negative electrode bodies 20 (20A and 20B) and 21 (21A and 21B) are disposed at symmetrical positions across a reference line R1 running in the up and down direction of the backrest 10.

The positive and negative electrode bodies 20 (20A and 20B) and 21 (21A and 21B) are each made of a stainless steel plate having a diameter of 80 mm and a thickness of 0.05 mm, and are fixed to the front surface of the backrest 10 with female and male hook-and-loop fasteners (not shown). A dimension between centers of the electrode bodies 20 and 21

(20A and 21A, and 20B and 21B) in a left and right direction is preferably set to 130 to 150 mm, and is set to 130 mm in the present embodiment. Also, a dimension between centers of the electrode bodies 20 and 21 (20A and 21A, and 20B and 21B) in an up and down direction is preferably set to 90 to 120 mm, and is set to 100 mm in the present embodiment. It is preferable that the electrode bodies 20 and 21 are arranged such that a heart of a person to be measured in a seated posture is positioned between a height position of the first channel 13A and a height position of the second channel 13B. In the present embodiment, a height dimension from an upper surface of a seat surface 9 to the centers of the positive and negative electrode bodies 20A and 21A of the first channel 13A is set to 400 mm. The positive and negative electrode bodies 20 (20A and 20B) and 21 (21A and 21B) may be made of a copper plate, a flexible printed circuit board whose surface is gold-plated, a conductive rubber plate, a woven fabric made of conductive fibers, or the like in addition to a stainless steel plate. Also, a shape is not limited to a circular shape, and may be an elliptical shape or a polygonal shape.

When a driver of a vehicle as a person to be measured leans on the backrest 10 while sitting on the seat surface 9, the positive and negative electrode bodies 20 (20A and 20B) and 21 (21A and 21B) of the electrocardiogram measurement units 13 and 13 of both the channels 13A and 13B are disposed on the back side of the body via clothes (see FIG. 4), and electric signals are detected by the positive and negative electrode bodies 20 (20A and 20B) and 21 (21A and 21B) constituting capacitive coupling electrodes.

The electric signal detected by the electrode bodies 20A and 21A of the first channel 13A is processed by the signal processing unit 22A to be an electrocardiographic signal. Specifically, the detected electric signal is converted into an electrocardiographic signal constructed by an analog signal amplified 100 times by the instrumentation amplifier 23A, and the relevant electrocardiographic signal is subjected to remove line noise and interference noise by the high-pass filter 26A and the low-pass filter 27A, and is further amplified 11 times by a differential amplifier 25A. Similarly, the electric signal detected by the electrode bodies 20B and 21B of the second channel 13B is processed by the signal processing unit 22B to be an electrocardiographic signal. Specifically, the detected electric signal is converted into an electrocardiographic signal constructed by an analog signal amplified 100 times by the instrumentation amplifier 23B, and the relevant electrocardiographic signal is subjected to remove line noise and interference noise by the high-pass filter 26B and the low-pass filter 27B, and is further amplified 11 times by a differential amplifier 25B.

The electrocardiographic signals constructed by the analog signals measured by the first and second channels 13A and 13B are converted into digital signals by the A/D converter 15. The electrocardiographic signals converted into the digital signals by the A/D converter 15 are transmitted to a system server 3 by wireless communication established between a wireless communication unit 16 and the communication line 5, and the system server 3 records and stores the acquired electrocardiographic signals in a built-in storage unit. In the A/D converter 15, the electrocardiographic signals constructed by the analog signals are converted into 8-bit or 16-bit digital signals. This is because a subsequent waveform analysis of an electrocardiographic signal is facilitated and a load on the wireless communication is reduced.

At the time of detecting electric signals, the inverting output unit 28A of the first channel 13A outputs an inverted signal obtained by inverting an in-phase signal of the electric signals input to the instrumentation amplifier 23A, and the relevant inverted signal is fed back to the positive electrode body 20A via the feedback amplifier 29A. As a result, an influence of in-phase signals of the electric signals detected by the electrode bodies 20A and 21A can be removed from the differential input, so that noise included in the electric signals detected by the electrode bodies 20A and 21A can be reduced by a so-called RLD (right-foot drive) method. Similarly, since the inverting output unit 28B of the second channel 13B outputs an inverted signal obtained by inverting the in-phase signal of the electrical signal input to the instrumentation amplifier 23B, and the relevant signal is fed back to the negative electrode body 21B via the feedback amplifier 29B, an influence of the in-phase signals of the electrical signals detected by the electrode bodies 20B and 21B can be removed from the differential input, so that noise included in the electrical signals detected by the electrode bodies 20B and 21B can be reduced by the RLD method.

As described above, in the present embodiment, since the inverted signals are input to the electrode bodies (the positive electrode body 20A and the negative electrode body 21B) of a different polarity present at a diagonal position among the four positive and negative electrode bodies 20 and 21 fixed to the backrest 10, the noise can be more accurately reduced.

Figure 5:
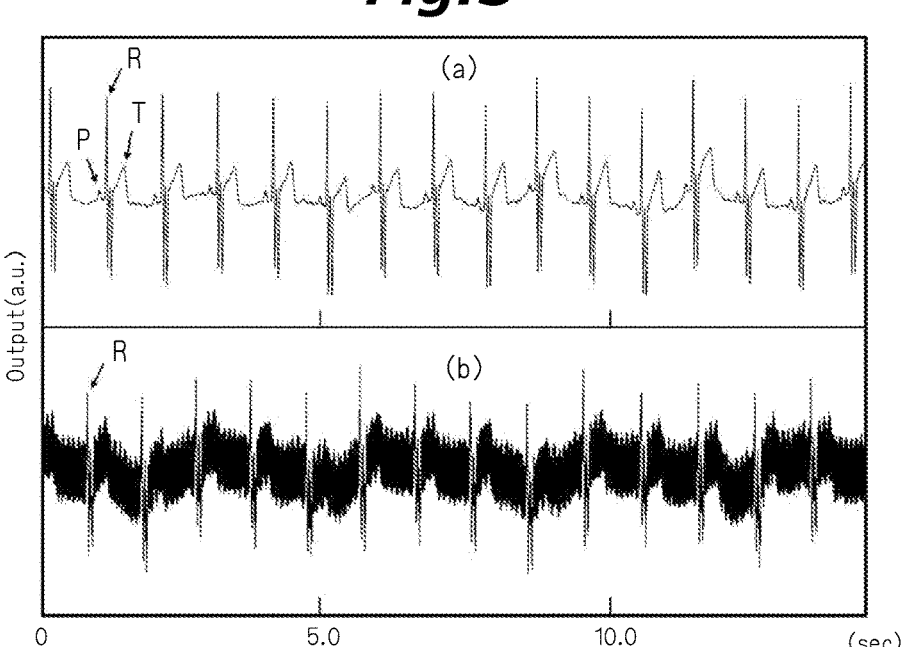
FIG. 5 shows waveforms of electrocardiographic signals on one side of two sets of electrocardiogram measurement units, in which (a) is a waveform of an electrocardiographic signal when the two sets of electrocardiogram measurement units perform a feedback of a signal amplification unit to an electrode body of a different polarity, and (b) is a waveform of an electrocardiographic signal when the two sets of electrocardiogram measurement units perform a feedback of the signal amplification unit to the electrode body of the same polarity.

FIG. 5(*a*) shows a waveform of an electrocardiographic signal obtained when the inverted signal is input to the electrode bodies of the different polarity, and FIG. 5(*b*) shows a waveform of an electrocardiographic signal obtained when the inverted signal is input to the electrode bodies of the same polarity. As apparent from the waveforms of both the electrocardiographic signals in (a) and (b), in the lower waveform (b), although a peak of an R wave is observed, clear peaks of a P wave and a T wave cannot be observed. On the other hand, in the upper waveform (a), clear peaks can be observed in all of the R wave, the P wave, and the T wave. Note that the P wave in a waveform of an electrocardiographic signal reflects an electrical excitation of an atrium, the R wave reflects an electrical excitation of a ventricle, and the T wave reflects a process in which cardiomyocytes of an excited ventricle are re-polarized.

Figure 4:
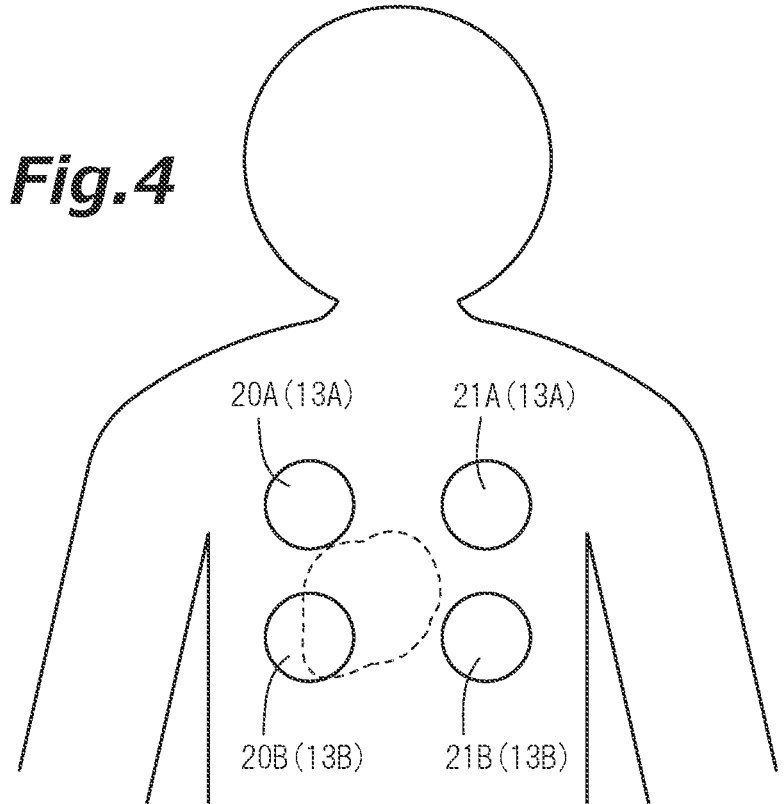
FIG. 4 is a rear view illustrating a relationship between the electrocardiographic signal measurement device and a contact part of a body.
Figure 6:
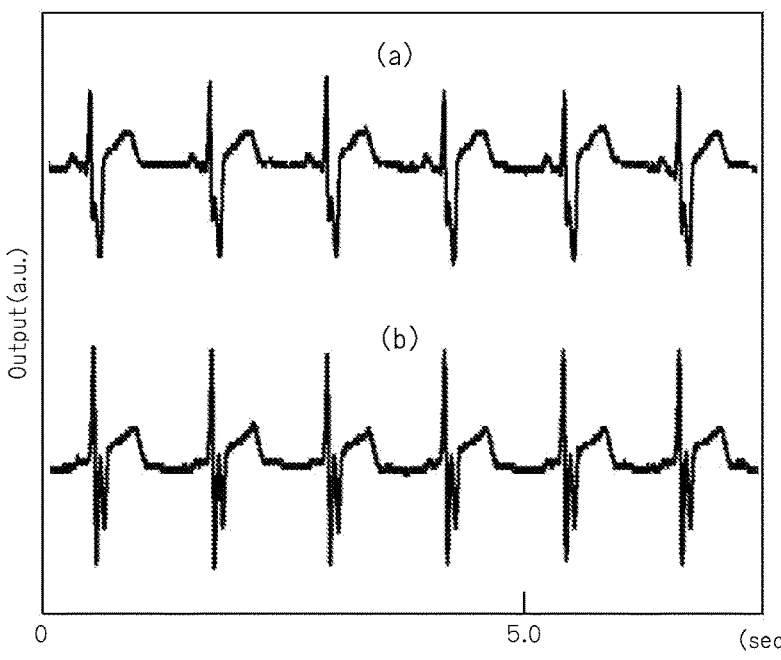
FIG. 6 is a diagram illustrating an example of waveforms of electrocardiographic signals measured by the electrocardiographic signal measurement device.

The electrocardiographic signals recorded in the system server 3 can be acquired by the terminal device 4, and FIG. 6 illustrates a portion of the electrocardiographic signals recorded in the system server 3, which is displayed as a waveform on the terminal device 4. An upper waveform (a) is a waveform of an electrocardiographic signal measured in the first channel 13A, and a lower waveform (b) is a waveform of an electrocardiographic signal measured in the second channel 13B. As shown in FIG. 4, in an arrangement form of the positive and negative electrode bodies 20 (20A and 20B) and 21 (21A and 21B) of the present embodiment, since the positive and negative electrode bodies 20B and 21B related to the second channel 13B are arranged at positions close to a heart of a person to be measured, although a peak value of the lower waveform (b) is high, it can be seen that the electrocardiographic signals having the substantially same waveforms are measured. In addition, the terminal device 4 can calculate an autonomic nerve index, a sympathetic nerve index, or the like derived from a waveform or a heartbeat variable by measuring a heartbeat interval from the acquired electrocardiographic signals and performing time domain analysis or frequency domain analysis. It is also possible to confirm a change in heart rate over time from electrocardiographic signals. For example, it is possible to prevent an occurrence of an accident or the like caused by poor physical condition in advance by constantly monitoring an electrocardiographic signal of a driver of a truck or a bus, and notifying the driver that an abnormal state has occurred when an abnormality is detected in the electrocardiographic signal.

As described above, the electrocardiographic signal measurement device of the present embodiment comprises the inverting output unit 28 that inverts the in-phase signals of the electrical signals from both the positive and negative electrode bodies 20 and 21 constituting the capacitive coupling electrodes and outputs the signals as the inverted signals, and the inverted signals output from the inverting output unit 28 are input to the positive and negative electrode bodies 20 and 21. Therefore, a noise reduction effect by a so-called RLD method is achieved, and thus a clearer electrocardiographic signal can be obtained. In addition, for example, in a mode in which an electrode body dedicated to the RLD is provided in addition to both the positive and negative electrode bodies 20 and 21, there is a possibility that the noise reduction effect by the RLD method is lost when a contact state between the electrode body dedicated to the RLD and a human body is released or the electrode body dedicated to the RLD is greatly separated from the human body. However, when an inverted signal is provided to the electrode bodies 20 and 21 constituting the capacitive coupling electrodes for measuring an electrocardiographic signal as in the present embodiment, the noise reduction effect by the RLD method is more stably exhibited without being affected by the contact state of the electrode body dedicated to the RLD or the like as described above, so that more stable and clear electrocardiographic signal can be obtained. In particular, since the two sets of electrode bodies 20 and 21 of the first and second channels 13A and 13B are arranged in the body portion of the person to be measured, even if any one of the electrode bodies interferes with the detection of the electric signal, it is possible to back up the detection of the electric signal by the other electrode body. Further, since the arrangement directions of the positive and negative electrode bodies 20 and 21 of the first and second channels 13A and 13B are made to coincide with each other, it is possible to detect electric signals having the same phase in both the channels 13A and 13B.

In addition, when the electrocardiogram measurement unit 13 in which the inverted signal from the inverting output unit 28 is input to the positive electrode body 20 is defined as the first channel 13A, and the electrocardiogram measurement unit 13 in which the inverted signal from the inverting output unit 28 is input to the negative electrode body 21 is defined as the second channel 13B, if both the channels 13A and 13B are comprised at the same time, the inverted signals can be applied to both the positive and negative electrode bodies 20 and 21. Therefore, the noise reduction effect by the RLD method is more reliably exhibited, and a clearer electrocardiographic signal can be obtained, as compared with a mode in which the inverted signal is applied only to one of the electrode bodies 20 and 21 (see FIG. 5(*a*)).

In addition, since the inverted signal from the inverting output unit 28A of the first channel 13A is input to the positive electrode body 20A, and the inverted signal from the inverting output unit 28B of the second channel 13B is input to the negative electrode body 21B, it is possible to apply the electric signal for noise reduction to a body surface in a wider range as compared with the case where the relevant electric signals are applied from the electrode bodies 20A and 21A adjacent to each other on the left and right, and it is possible to improve an SN ratio by reducing the noise of the electric signals detected by the positive and negative electrode bodies 20 (20A and 20B) and 21 (21A and 21B). As a result, according to the electrocardiographic signal measurement device 2 of the present embodiment, it is also possible to stably measure the electrocardiographic signals, and further to obtain the clear electrocardiographic signals by reducing the detection of noise.

The positive electrode bodies 20 (20A and 20B) of the first and second channels 13A and 13B are arranged at one offset position in the left and right direction with respect to the reference line R1 running in the up and down direction of the backrest 10 (base 7), the negative electrode bodies 21 (21A and 21B) of the first and second channels 13A and 13B are arranged at the other offset position in the left and right direction with respect to the reference line R1, and the positive and negative electrode bodies 20A and 20B constituting the first channel 13A and the positive and negative electrode bodies 21A and 21B constituting the second channel 13B are alternately arranged in the up and down direction. Therefore, the positive and negative electrode bodies 20 and 21 to which the inverted signal is applied do not offset to either the left and right direction or the up and down direction, the inverted signal can be applied to a wider range of the human body, and noise can be further reduced to improve the SN ratio. Therefore, the electrocardiographic signals can be stably measured, and the clearer electrocardiographic signals can be obtained. Since the arrangement directions of the positive and negative electrode bodies 20 and 21 of the first and second channels 13A and 13B are made to coincide with each other, it is possible to detect the electric signals having the same phase in both the channels 13A and 13B.

Since the signal processing unit 22 comprises the noise removal unit 24 that removes noise included in the electrocardiographic signal output from the signal amplification unit 23, it is possible to remove the noise from the electrocardiographic signal amplified by the signal amplification unit 23 and clarify the electrocardiographic signal.

Since the positive and negative electrode bodies 20 and 21 of the first and second channels 13A and 13B are provided on the front surface of the backrest 10 of the chair 8, the person to be measured can measure his/her electrocardiographic signal only by sitting on the chair 8 and leaning against the backrest 10. Therefore, it is possible to stably measure an electrocardiographic signal of a driver who is driving a vehicle or an employee who is working in an office under the condition that a physical burden is further suppressed.

In addition, the electrocardiographic signal measurement system of the present embodiment is configured by comprising the electrocardiographic signal measurement device 2 that measures the electrocardiographic signal, the system server 3 that is connected to the electrocardiographic signal measurement device 2 via the communication line 5 and records the electrocardiographic signal measured by the electrocardiographic signal measurement device 2, and the terminal device 4 that is connected to the system server 3 via the communication line 5 and is capable of acquiring the electrocardiographic signal recorded in the system server 3. Since the electrocardiographic signal measurement device 2 comprises the wireless communication unit 16 for establishing wireless communication with the communication line 5, it is possible to remotely monitor the electrocardiographic signal of the person to be measured. Therefore, for example, when the person to be measured is a driver of a truck or a bus, it is possible to easily check electrocardiographic signals while driving the vehicle at a remote place such as a company office.

In addition, when this electrocardiographic signal measurement device is used for measuring an electrocardiographic signal, it is possible to stably obtain a clear electrocardiographic signal, and thus it is possible to contribute to the goal 3 (health and welfare for all people) of the sustainable development goals (SDGs) proposed by the United Nations.

Figure 7:
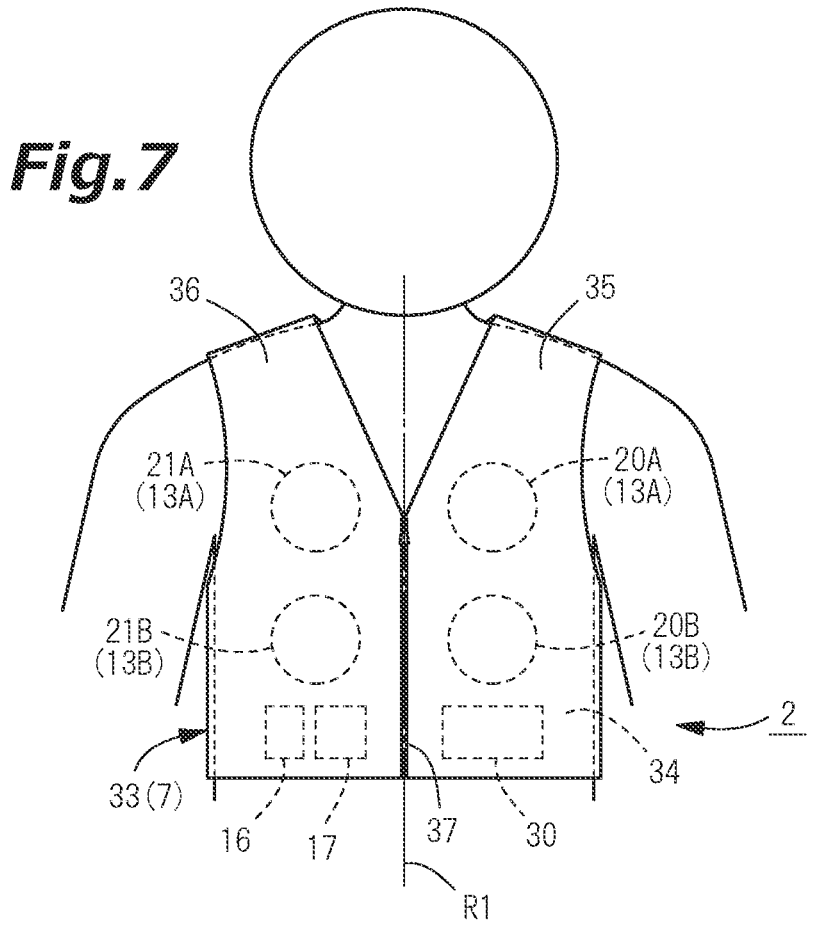
FIG. 7 shows a second embodiment of the present invention, and is a front view of a mode in which an electrocardiographic signal measurement device is provided on a vest.
Figure 8:
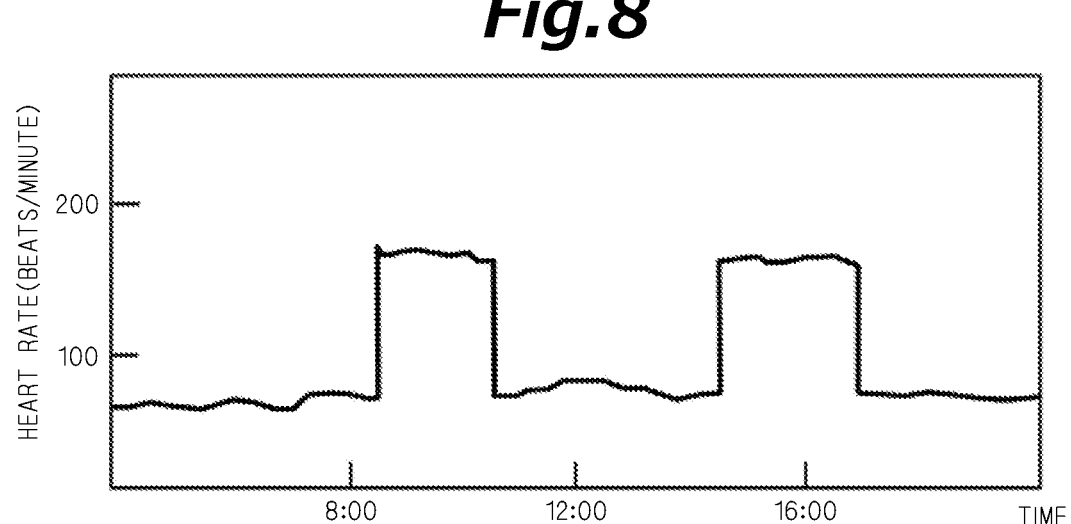
FIG. 8 is a trend graph obtained by plotting a long-time average heart rate calculated from an electrocardiographic signal obtained by the electrocardiographic signal measurement device.

(Second embodiment) FIGS. 7 and 8 show a second embodiment of the present invention. The present embodiment is different from the first embodiment in that the base 7 is used as a vest (upper garment) 33, and the electrocardiographic signal measurement device 2 is provided in the vest 33. The vest 33 comprises a back body 34, and left and right front bodies 35 and 36, and the left and right front bodies 35 and 36 can be opened and closed with a zipper 37. On an inner surface of the left front body 35, the positive electrode body 20A of the first channel 13A and the positive electrode body 20B of the second channel 13B are arranged in the up and down direction, and an electrocardiogram measurement circuit box 30 in which the signal processing units 22A and 22B and the like are accommodated is fixed below the positive electrode body 20B. Also, on an inner surface of the right front body 36, the negative electrode body 21A of the first channel 13A and the negative electrode body 21B of the second channel 13B are arranged in the up and down direction, and further a wireless communication unit 16 and a power supply unit 17 are fixed below the negative electrode body 21B. Since the other points are similar to those of the first embodiment, the same members are denoted by the same reference numerals, and the descriptions thereof will be omitted.

When a person to be measured wears a vest 33, the positive and negative electrode bodies 20 (20A and 20B) and 21 (21A and 21B) of both the channels 13A and 13B can be disposed on a front side of the body portion, that is, on a chest, and the electrocardiographic signal can be measured regardless of an action or posture of the person to be measured. Since the electrocardiographic signal measurement device 2 detects an electrical signal of a body portion using the capacitive coupling electrode, the electrocardiographic signal can be measured from above the garment in a non-invasive manner.

An example is shown in which the vest 33 provided with the electrocardiographic signal measurement device 2 is used for a detection of paroxysmal atrial fibrillation. A person under examination was a 70 year old male with hypertension suspected of paroxysmal atrial fibrillation and a basal disease of diabetes, and was observed the course of resting indoors while wearing the vest 33 of this example from above underwear. Measurements of electrocardiographic signals were carried out from 0:00 AM to 24 hours (until 0:00 AM the next day). From the electrocardiographic signals obtained by the measurements, heart rates were averaged over a moving time of 5 seconds, and this was plotted against time to obtain a trend graph of a long-time average heart rate as shown in FIG. 8. FIG. 8 illustrates a graph from 4:00 AM to 8:00 PM. From the graph, the heart rates of the person under examination at rest were 70 to 80 beats per minute, and typical signs of paroxysmal atrial fibrillation in which an abnormal value of a heart rate including atrial fibrillation of 150 beats per minute or more continued for 1 hour or more could be observed twice.

As described above, according to the present embodiment, since the positive and negative electrode bodies 20 and 21 can be easily disposed on the chest (body portion) only by wearing the vest 33, it is possible to suppress the burden on the person to be measured even in the case of long-term measurement of the electrocardiographic signals. In addition, there is also an advantage that the electrocardiographic signals can be measured even in daily life, driving of a vehicle, or the like without limitation of behavior.

In the above embodiment, the positive and negative electrode bodies 20A and 21A of the first channel 13A are arranged on the upper side of the front surface of the backrest 10, and the positive and negative electrode bodies 20B and 21B of the second channel 13B are arranged on the lower side, but the upper and lower sides may be reversed.

Figure 9:
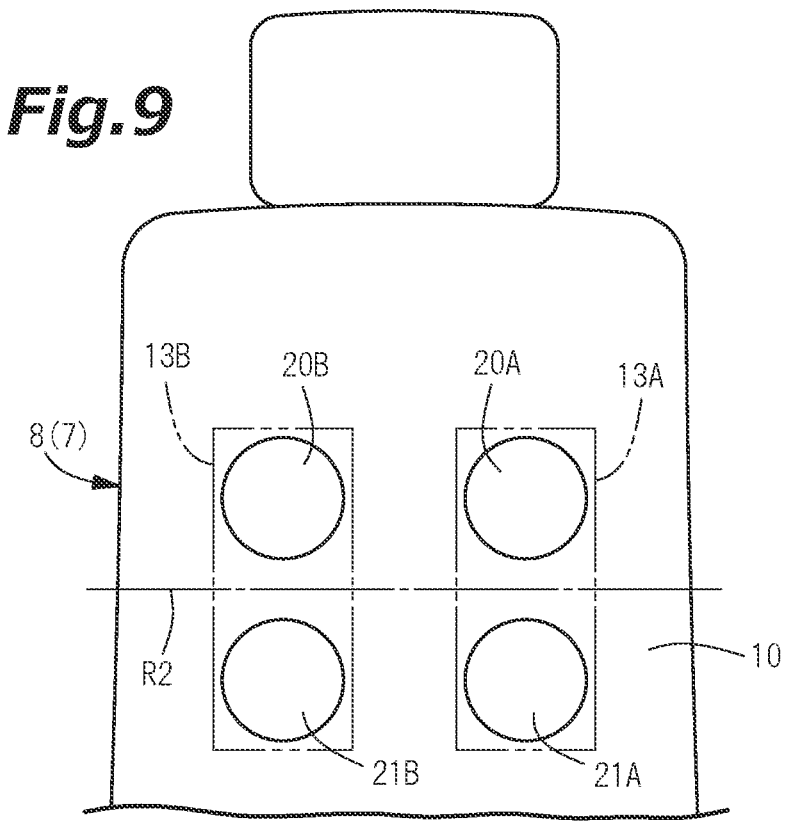
FIG. 9 shows a third embodiment of the present invention and is a view showing another arrangement mode of an electrode body.

Also, as shown in FIG. 9, the positive and negative electrode bodies 20A and 21A of the first channel 13A may be arranged vertically on one of the left and right sides (the left side in the illustrated example) of the front surface of the backrest 10, and the positive and negative electrode bodies 20B and 21B of the second channel 13B may be arranged vertically on the other side (the right side in the illustrated example).

Specifically, the positive electrode body 20A of the first channel 13A is arranged on an upper left side of the backrest 10, and the negative electrode body 21A is arranged on a lower left side of the backrest 10. The positive electrode body 20B of the second channel 13B is arranged on a lower left side of the backrest 10, and the negative electrode body 21B is arranged on a lower right side of the backrest 10.

In addition, as shown in FIG. 9, height positions of the positive electrode bodies 20A and 20B of the first channel 13A and the second channel 13B located on the upper side are set to substantially the same position. Similarly, height positions of the negative electrode bodies 21A and 21B of the first channel 13A and the second channel 13B located on the lower side are set to substantially the same position. As described above, in the backrest 10, the positive and negative electrode bodies 20A and 21A of the first channel 13A and the positive and negative electrode bodies 20B and 21B of the second channel 13B are arranged side by side in a left-right direction. Also, the positive and negative electrode bodies 20 (20A and 20B) and 21 (21A and 21B) are arranged at symmetrical positions across a reference line R2 running in the horizontal direction of the backrest 10.

The positive electrode bodies 20 (20A and 20B) for constructing the first and second channels 13A and 13B are arranged at one offset position in the up and down direction with respect to the reference line R2 running in the horizontal direction of the backrest 10 (base 7); the negative electrode bodies 21 (21A and 21B) constructing the first and second channels (13A and 13B) are arranged at the other offset position in the up and down direction with respect to the reference line R2; and the positive and negative electrode bodies 20A and 21A for constructing the first channel 13A and the positive and negative electrode bodies 20B and 21B for constructing the second channel 13B are arranged side by side in the left-right direction. Therefore, the positive and negative electrode bodies 20 and 21 to which the inverting signals are applied do not offset to either the left-right direction or the up and down direction, the inverting signals can be applied to a wider range of the human body, and noise can be further reduced to improve the SN ratio. Therefore, the electrocardiographic signals can be stably measured, and the clearer electrocardiographic signals can be obtained. Since the arrangement directions of the positive and negative electrode bodies 20 and 21 of the first and second channels 13A and 13B are made to coincide with each other, it is possible to detect the electric signals having the same phase in both the channels 13A and 13B.

Although the electrocardiogram measurement unit 13 is configured to include two sets of the first and second channels 13A and 13B, it is also possible to provide three or more sets of channels as long as there is a space to dispose. The noise removal unit 24 may comprise either the high-pass filter 26 or the low-pass filter 27. It may be a mode that the electrocardiographic signal measurement device 2 and the system server 3 communicate with each other in a wired manner.

REFERENCE SIGNS LIST

1 Electrocardiographic signal measurement system
2 Electrocardiographic signal measurement device
3 Recording server (system server)
4 Terminal device
5 Communication line
7 Base
8 Chair (seat)
10 Backrest
13 Electrocardiogram measurement unit
13A First channel
13B Second channel
16 Wireless communication unit
20(20A·20B) Positive electrode body
21(21A·21B) Negative electrode body
22 Signal processing unit
23 Signal amplification unit (instrumentation amplifier)
24 Noise removal unit
28 Inverting output terminal
33 Upper garment (vest)

The invention claimed is:

1. A multi-channel type electrocardiographic signal measurement device including:
    a plurality of electrocardiogram measurement units that measure an electrocardiographic signal, wherein each of the electrocardiogram measurement units comprises:
        a pair of positive and negative electrode bodies constituting capacitive coupling electrodes and configured to be arranged in a non-contact state with a human body;
        a signal amplification unit that amplifies an electrical signal from both the electrode bodies and outputs the amplified electrical signal as an electrocardiographic signal ; and
        an inverting output unit that inverts an in-phase signal of the electrical signal from both the electrode bodies and outputs the inverted signal, and wherein the inverted signal output from the inverting output unit is input to one of the positive and negative electrode bodies; and
    the electrocardiographic signal measurement device comprises two channels simultaneously, wherein one of the plurality electrocardiogram measurement units through which the inverted signal from the inverting output unit is input to the positive electrode body is a first channel, and another of the plurality of electrocardiogram measurement units through which the inverted signal from the inverting output unit is input to the negative electrode body is a second channel.

2. The electrocardiographic signal measurement device according to claim 1, the electrocardiographic signal measurement device comprising a base that supports the human body or is worn on the human body, and on which the electrode bodies are mounted, wherein the positive electrode bodies of the first and second channels are arranged at one offset position in a left and right direction with respect to a reference line running in an up and down direction of the base, the negative electrode bodies of the first and second channels are arranged at the other offset position in the left and right direction with respect to the reference line, and the positive and negative electrode bodies of the first channel, and the positive and negative electrode bodies of the second channel are alternately arranged in the up and down direction.

3. The electrocardiographic signal measurement device according to claim 2, wherein the electrocardiogram measurement unit comprises a noise removal unit that removes noise included in the electrocardiographic signal output from the signal amplification unit.

4. The electrocardiographic signal measurement device according to claim 2, wherein the base is a backrest of a chair, and the positive and negative electrode bodies of the electrocardiogram measurement unit are provided on a front surface of the backrest.

5. An electrocardiographic signal measurement system comprising: the electrocardiographic signal measurement device according to claim 4 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

6. The electrocardiographic signal measurement device according to claim 2, wherein the base is an upper garment worn on an upper half body of the human body, and the positive and negative electrode bodies of the electrocardiogram measurement unit are provided on the upper garment.

7. An electrocardiographic signal measurement system comprising: the electrocardiographic signal measurement device according to claim 6 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

8. An electrocardiographic signal measurement system comprising: the electrocardiographic signal measurement device according to claim 2 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

9. The electrocardiographic signal measurement device according to claim 1, the electrocardiographic signal measurement device comprising a base that supports the human body or is worn on the human body, and on which the electrode bodies are mounted, wherein the positive electrode bodies and for constructing the first and second channels are arranged at one offset position in the up and down direction with respect to a reference line running in a horizontal direction of the base, the negative electrode bodies for constructing the first and second channels are arranged at the other offset position in the up and down direction with respect to the reference line, and the positive and negative electrode bodies for constructing the first channel, and the positive and negative electrode bodies for constructing the second channel are alternately arranged in the left and right direction.

10. The electrocardiographic signal measurement device according to claim 9, wherein the electrocardiogram measurement unit comprises a noise removal unit that removes noise included in the electrocardiographic signal output from the signal amplification unit.

11. The electrocardiographic signal measurement device according to claim 9, wherein the base is a backrest of a chair, and the positive and negative electrode bodies of the electrocardiogram measurement unit are provided on a front surface of the backrest.

12. An electrocardiographic signal measurement system comprising: the electrocardiographic signal measurement device according to claim 11 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

13. The electrocardiographic signal measurement device according to claim 9, wherein the base is an upper garment worn on an upper half body of the human body, and the positive and negative electrode bodies of the electrocardiogram measurement unit are provided on the upper garment.

14. An electrocardiographic signal measurement system comprising: the electrocardiographic signal measurement device according to claim 13 for measuring an electrocardiographic signal ; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

15. An electrocardiographic signal measurement system comprising: the electrocardiographic signal measurement device according to claim 9 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

16. The electrocardiographic signal measurement device according to claim 1, wherein the electrocardiogram measurement unit comprises a noise removal unit that removes noise included in the electrocardiographic signal output from the signal amplification unit.

17. The electrocardiographic signal measurement device according to claim 16, wherein the base is a backrest of a chair, and the positive and negative electrode bodies of the electrocardiogram measurement unit are provided on a front surface of the backrest.

18. The electrocardiographic signal measurement device according to claim 16 wherein the base is an upper garment worn on an upper half body of the human body, and the positive and negative electrode bodies of the electrocardiogram measurement unit are provided on the upper garment.

19. An electrocardiographic signal measurement system comprising: the electrocardiographic signal measurement device according to claim 16 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

20. An electrocardiographic signal measurement system comprising: the electrocardiographic signal measurement device according to claim 1 for measuring an electrocardiographic signal; a recording server that is connected to the electrocardiographic signal measurement device via a communication line and records the electrocardiographic signal measured by the electrocardiographic signal measurement device; and a terminal device that is connected to the recording server via the communication line and is capable of acquiring the electrocardiographic signal recorded in the recording server, wherein the electrocardiographic signal measurement device comprises a wireless communication unit for establishing wireless communication with the communication line.

* * * * *